United States Patent
Rohrer et al.

(10) Patent No.: US 10,675,225 B2
(45) Date of Patent: Jun. 9, 2020

(54) OPTICALLY DIFFUSING PARTICLES

(71) Applicant: Sun Chemical Corporation, Parsippany, NJ (US)

(72) Inventors: Anthony Rohrer, Centerville, OH (US); Jonathan Doll, Cincinnati, OH (US); Kelly Ann Dobos, Cincinnati, OH (US)

(73) Assignee: Sun Chemical Corporation, Parsippany, NJ (US)

( * ) Notice: Subject to any disclaimer, the term of this patent is extended or adjusted under 35 U.S.C. 154(b) by 48 days.

(21) Appl. No.: 16/037,240

(22) Filed: Jul. 17, 2018

(65) Prior Publication Data

US 2018/0344586 A1    Dec. 6, 2018

Related U.S. Application Data

(63) Continuation of application No. PCT/US2017/013785, filed on Jan. 17, 2017.

(60) Provisional application No. 62/280,910, filed on Jan. 20, 2016.

(51) Int. Cl.
*A61K 8/02* (2006.01)
*A61Q 1/02* (2006.01)
*A61K 8/25* (2006.01)

(52) U.S. Cl.
CPC ............ *A61K 8/0258* (2013.01); *A61K 8/025* (2013.01); *A61K 8/0245* (2013.01); *A61K 8/0254* (2013.01); *A61K 8/25* (2013.01); *A61Q 1/02* (2013.01); *A61K 2800/412* (2013.01); *A61K 2800/43* (2013.01); *A61K 2800/621* (2013.01); *A61K 2800/651* (2013.01)

(58) Field of Classification Search
None
See application file for complete search history.

(56) References Cited

U.S. PATENT DOCUMENTS

| | | |
|---|---|---|
| 5,320,834 A | 6/1994 | Ounanian et al. |
| 6,511,536 B1 | 1/2003 | Noguchi et al. |
| 6,511,672 B2 | 1/2003 | Tan et al. |
| 7,709,013 B2 | 5/2010 | Patel |
| 8,715,407 B2 | 5/2014 | Schumacher et al. |
| 9,250,179 B2 | 2/2016 | Schmidt et al. |
| 2005/0048016 A1 | 3/2005 | Lebreton et al. |
| 2005/0074473 A1 | 4/2005 | Kosbach et al. |
| 2005/0220739 A1 | 10/2005 | Dreher et al. |
| 2008/0219940 A1 | 9/2008 | Chevalier et al. |
| 2010/0297045 A1 | 11/2010 | Kaupp et al. |

FOREIGN PATENT DOCUMENTS

| | | |
|---|---|---|
| WO | WO 2011/082019 A1 | 7/2011 |
| WO | WO 2015/024615 A1 | 2/2015 |

OTHER PUBLICATIONS

"MDA-A-163-01 Face powder with RonaFlair Soft focus fillers," Merck, Jul. 2003, downloaded from https://www/ulprospector.com/en/eu/PersonalCare/Detail/824/331892/Face-Powder-with-RonaFlair-Soft-Focus-Fillers-Formulation-MDA-A-163-01?doc=1197120&st=20, on Mar. 2, 2017, XP002767768, 1 pg.
"RonaFlair® Flair up your beauty products with RonaFlair® Functional Fillers," Merck, Nov. 2011, downloaded from https://www.ulprospector.com/documents/1192168.pdf?bs=824&b=108232&st=20, on Mar. 2, 2017, XP002767769, 26 pgs.
U.S. Appl. No. 62/280,910, filed Jan. 20, 2016.

*Primary Examiner* — Nannette Holloman
(74) *Attorney, Agent, or Firm* — Frost Brown Todd LLC

(57) ABSTRACT

A soft-focus composition comprises particles. The particles comprise a substrate with a metal oxide coating. The metal oxide coating covers from about 50% to about 75% of the surface area of the substrate. The particles have a span of from about 0.1 to about 2.1. From about 50% to about 75% of the particles are platelet shaped and the remainder are at least one different shape. This soft-focus composition can be used in cosmetic and personal care formulations to impart a soft-focus effect on the skin to hide fine lines and blemishes while allowing the natural glow of the skin to shine through.

12 Claims, 6 Drawing Sheets

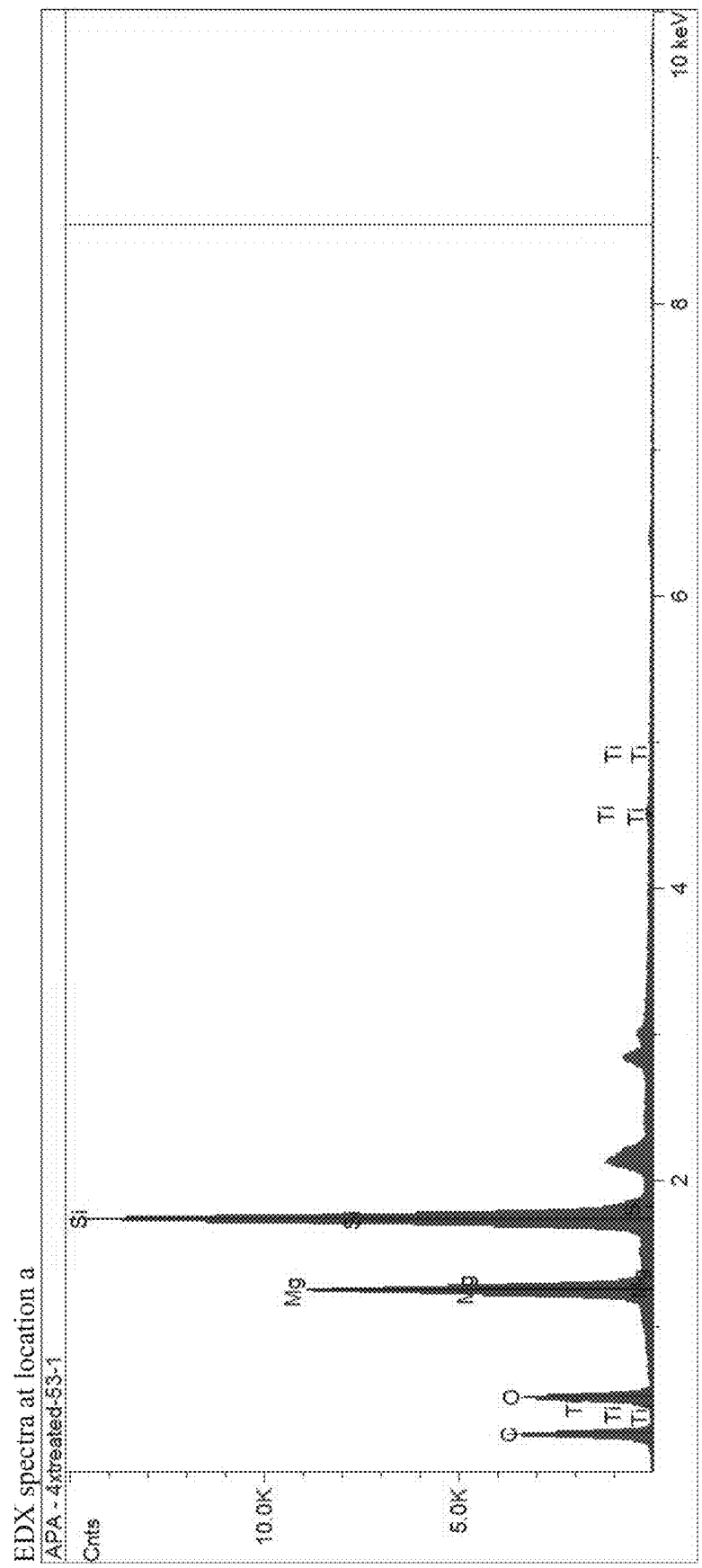

OPTICALLY DIFFUSING PARTICLES

CROSS REFERENCE TO RELATED APPLICATIONS

The present application hereby claims the benefit of PCT/US2017/013785, filed on Jan. 17, 2017, which claimed the benefit of the provisional patent application of the same title, Ser. No. 62/280,910, filed on Jan. 20, 2016, the disclosure of which is herein incorporated by reference in its entirety.

BACKGROUND

In cosmetics applications, there is a need for materials that can give the skin a smooth appearance by hiding or blurring the appearance of fine lines and wrinkles, while reducing any color irregularities due to hyper- or hypo-pigmentation. The described effect is known as "soft-focus." There are a number of pigment and filler types, as well as cosmetic formulations, that claim to impart soft-focus properties, including materials such as boron nitride and elastomeric silicone particles, among others. Generally, a blend of pigments is used, as in U.S. Pat. Nos. 6,511,672, and 7,709,013.

Layered pigments have been suggested for us as soft-focus pigments in certain applications (U.S. Pat. Nos. 5,320,834; 6,511,536; 6,511,672; US 2005/0220739; US 2008/0219940; and U.S. Pat. No. 7,709,013). The layered pigments are composed of a smooth, platelet-shaped or spherical substrate that is coated with one or more layers of a metal oxide. These pigments can have a large amount of diffuse light transmission. A significant drawback of layered platelet-shaped pigments is that they make the skin appear glossy, making wrinkles and blemishes more prevalent instead of blurred. A major drawback of multilayer spherical pigments is that they are difficult to make at a high yield, therefore limiting them to high value, expensive applications.

Many of the pigments used to impart soft-focus are made by lengthy and difficult manufacturing procedures, causing the price to be high. This limits their application to high-end specialty facial creams and lotions and does not enable them to be used in mass-market products like body lotions. Therefore, there is a need in the personal care industry for a soft-focus pigment system that can be used to impart soft-focus in body lotions.

BRIEF SUMMARY

A soft-focus composition comprises particles. The particles comprise a substrate with a metal oxide coating. The metal oxide coating covers from about 50% to about 75% of the surface area of the substrate. The particles have a span of from about 0.1 to about 2.1. From about 50% to about 75% of the particles are platelet shaped and the remainder are at least one different shape.

These and other objects and advantages shall be made apparent from the accompanying drawings and the description thereof.

BRIEF DESCRIPTION OF THE FIGURES

The accompanying drawings, which are incorporated in and constitute a part of this specification, illustrate embodiments, and together with the general description given above, and the detailed description of the embodiments given below, explain the principles of the present disclosure.

DETAILED DESCRIPTION

Figure 1:
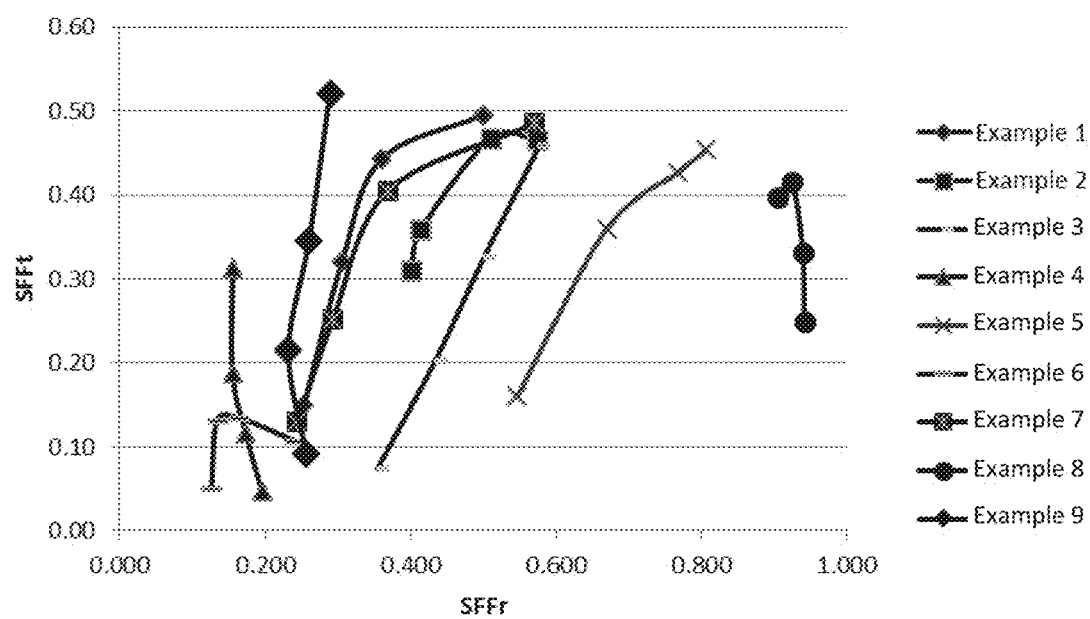
FIG. 1 is a graph of the relationship between the calculated $SFF_R$ and $SFF_T$ values for the various materials at each loading. An area near the middle of graph correlates to the most apparent soft-focus effect. There, the diffuse and total transparencies are maximized and the uniform scattering of reflected light is at its most natural appearance. The graph shows that it is not the $SFF_R$ or $SFF_T$ individually that produce a desirable soft-focus affect, but rather a ratio of the two parameters.
Figure 2:
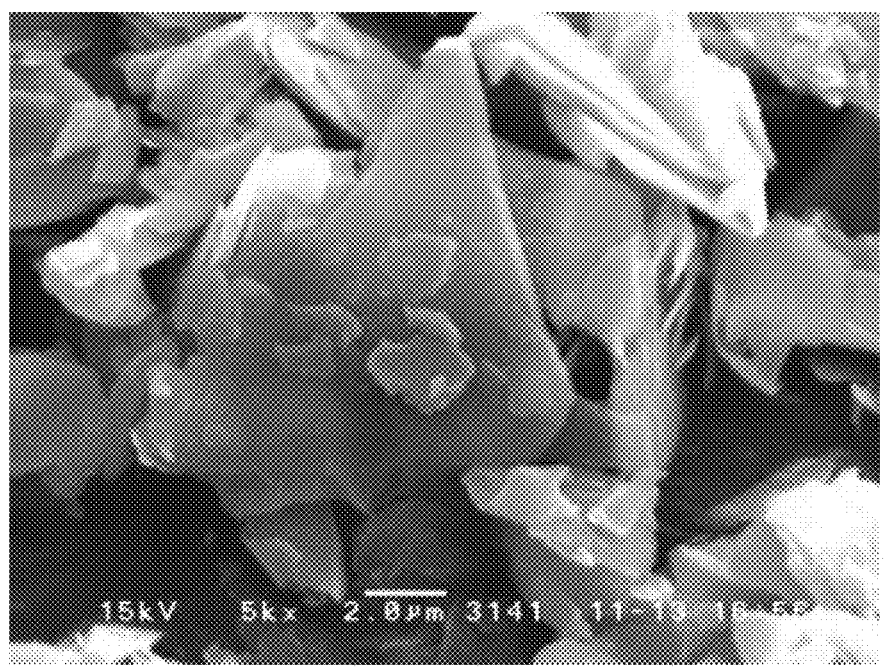
FIG. 2 is a Scanning Electron Microscope (SEM) image of Comparative Example 5 showing a mixture of platelets and irregular particles at a 5 kx magnification.
Figure 3:
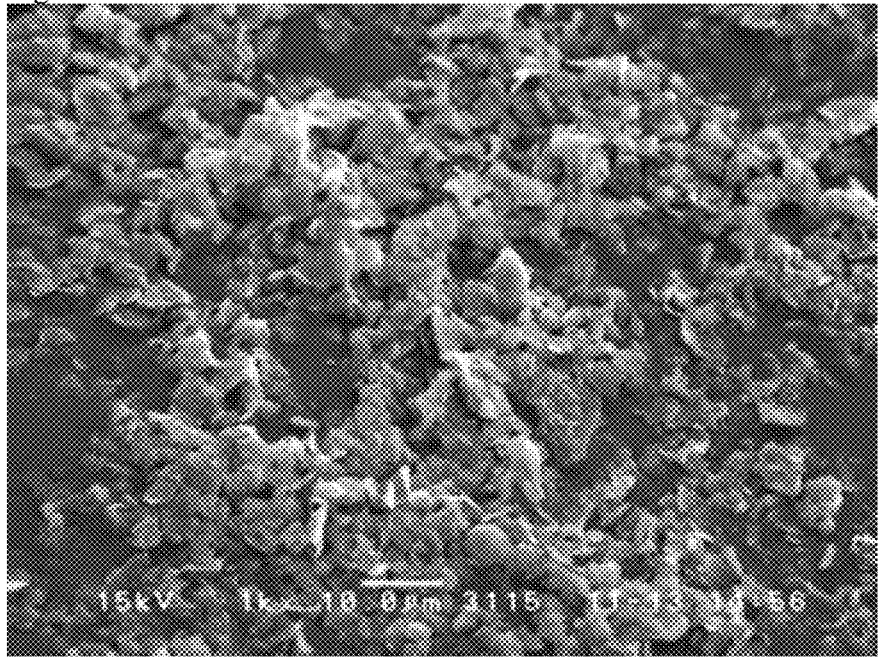
FIG. 3 is a SEM image of Comparative Example 5 showing a mixture of platelets and irregular particles at a 1 kx magnification.
Figure 4:
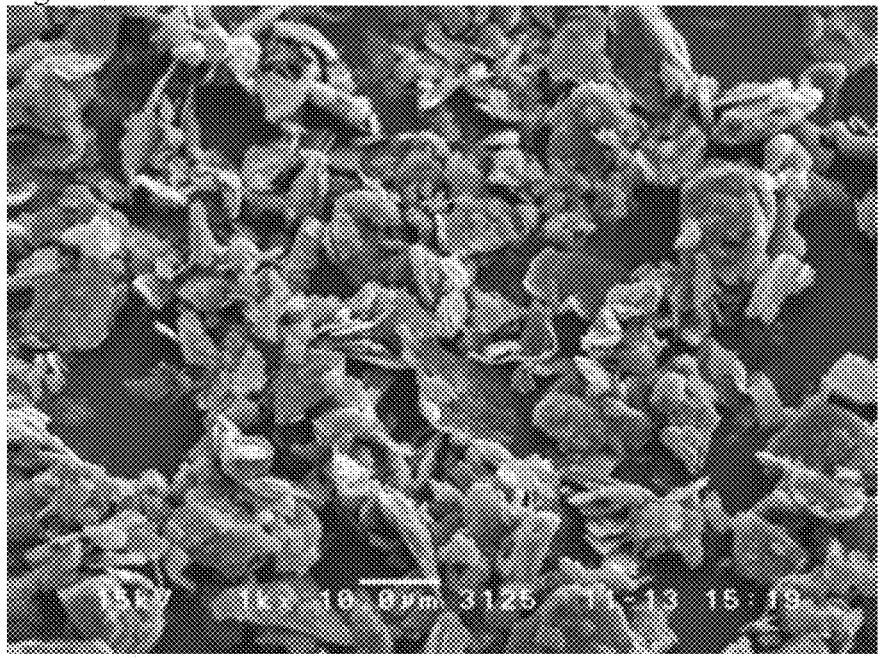
FIG. 4 is a SEM image of Example 2 at a 1 kx magnification.
Figure 5:
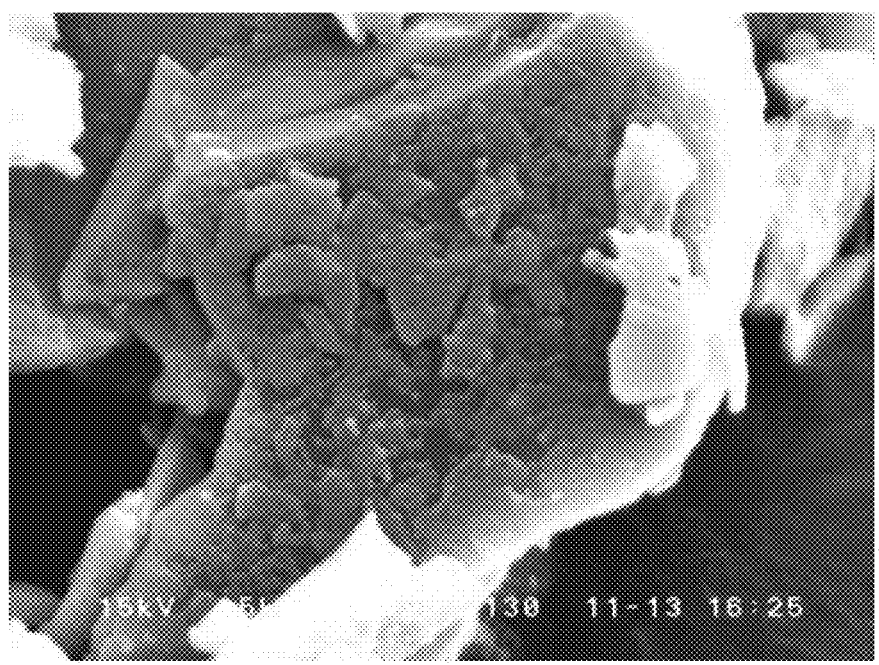
FIG. 5 is a SEM image of Example 2 at a 5 kx magnification.
Figure 6:
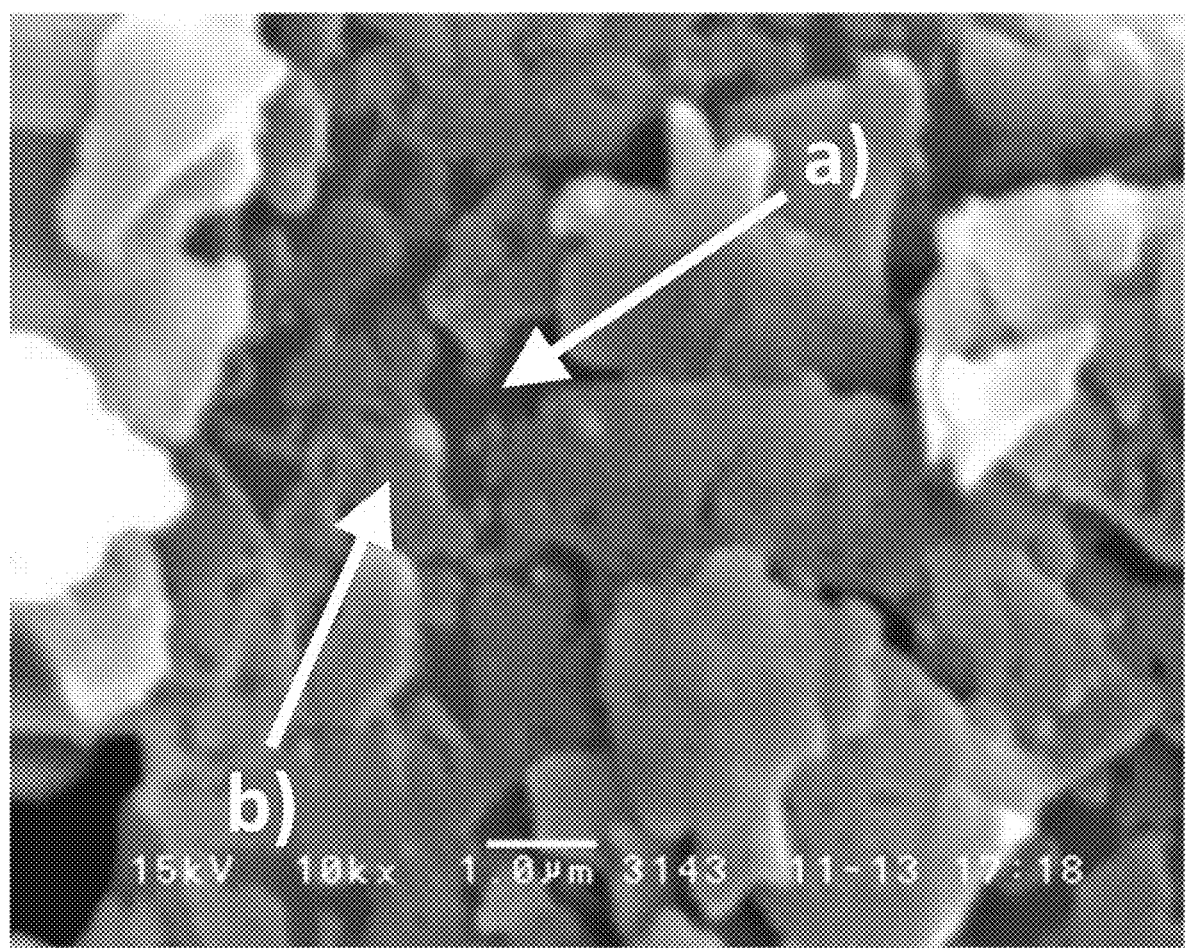
FIG. 6 is an SEM of the particles in Example 2 with EDX (Energy Dispersion X-ray spectroscopy) spectra of locations a) the uncoated (dark) region and b) the coated (light) region of the particle, which are shown in FIGS. 6A and 6B, respectively.
Figure 6B:
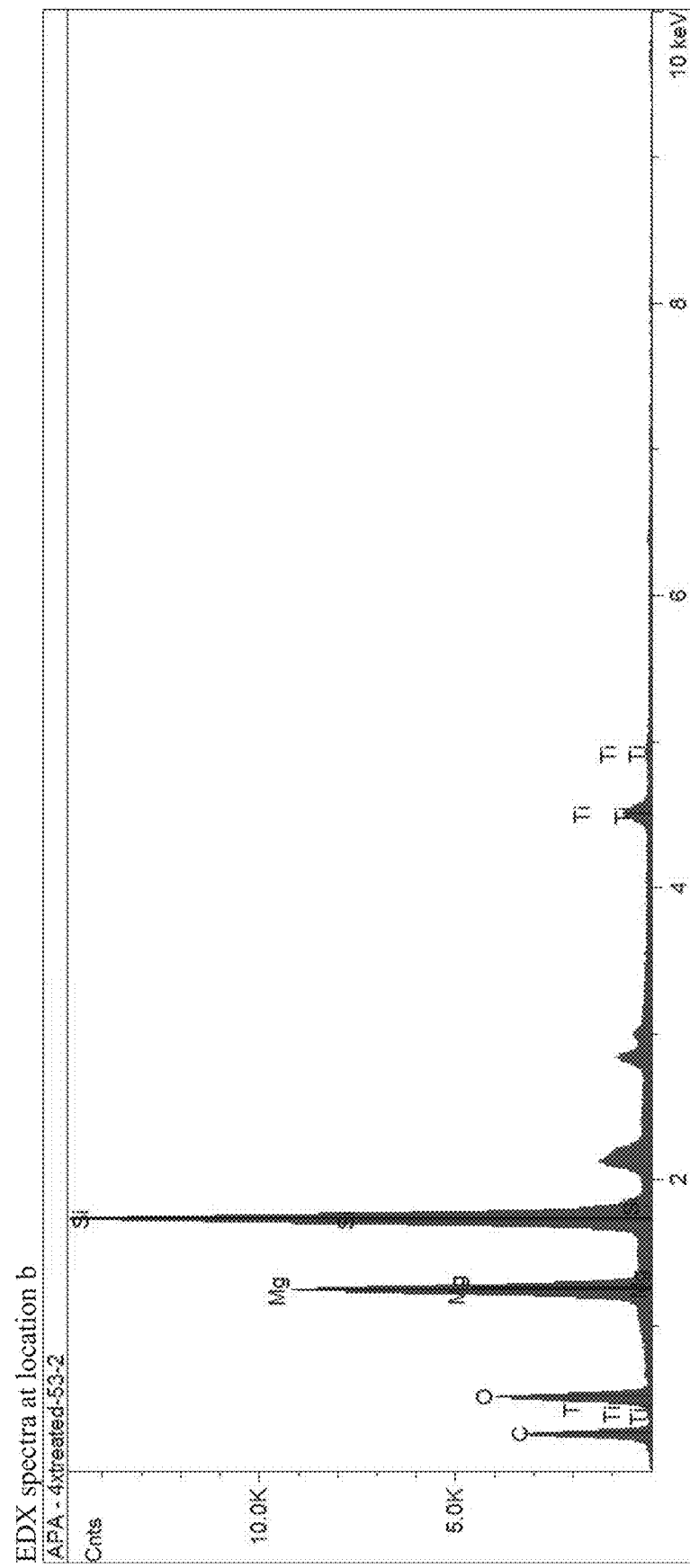

It has been surprisingly discovered that a composition comprising irregular particles, which are partially coated with a metal oxide, has exceptionally high soft-focus properties. This composition may be used in personal care products to give desirable soft-focus properties to hide fine lines and wrinkles.

This soft-focus composition does not require the use of multiple particles or pigments to get the right blend of optical properties for a soft-focus effect. In some embodiments, a single particle or type of particle with optical properties is used in the composition. A soft-focus effect is not normally found in a homogeneous soft-focus system with only a single particle or pigment with optical properties. The prior composition used a blend of materials to achieve soft-focus properties (U.S. Pat. No. 6,511,672; US 2005/0048016; US 2005/0074473; US 2005/0220739; US 2008/0219940; and U.S. Pat. No. 7,709,013). For example, U.S. Pat. No. 6,511,672 describes a multilayer platelet pigment that is blended with another platelet pigment that has been treated with smaller, spherical particles to create an irregular surface. U.S. Pat. No. 6,511,672 describes a low to high refractive index multilayer particle blended with transparent spherical polymers to create a soft-focus effect. In the these cases, a combination of multilayer, platelet-shaped pigments and other materials with irregular surfaces are used to create a soft-focus effect, i.e., soft-focus is not achieved in an unblended system.

The soft-focus composition comprises particles. The particles comprise a substrate with a metal oxide coating. The metal oxide coating covers from about 50% to about 75% of the surface area of the substrate. The particles have an average surface roughness of from about 1 nm to about 50 nm. About 50% to about 75% of the particles are platelet shaped and the remainder are at least one different shape.

The metal oxide coating of the particle does not cover the complete surface of the substrate. The coating may cover from about 50% to about 75% of the surface of the substrate, such as about 30% to about 85%, about 50% to about 75%, and about 60% to about 75%. In some embodiments, the metal oxide has a refractive index of greater than 2.

The metal oxide coating may be a single layer or multiple layers. If there are multiple layers they may be of the same metal oxide or of different metal oxides. In addition, the metal oxide layer may be further coated with layers of other materials. In some embodiments, the metal oxide layers are about 5 to about 75% of the total particle mass, such as about 50% to about 75%, about 10% to about 50%, and about 15% to about 30%. The thickness of a metal oxide coating layer is about 10 nm to about 1000 nm, such as about 30 nm to about 1000 nm, about 30 nm to about 600 nm, and about 40 nm to about 150 nm.

Examples of metal oxides include, but are not limited to: aluminum oxide, bismuth oxide, cerium oxide, chromium oxide, iron (II) oxide, iron (II, III) oxide, iron (III) oxide, magnesium silicate, silicon dioxide, titanium dioxide, zinc oxide, zirconium oxide, and mixtures or alloys thereof.

The substrate is a mixture of platelet shaped particles and at least one different shape. Examples of the other shape include, but are not limited to spheroids, cylinders, pyramid, polygons, potato-shaped, octahedral, hedgehog, and star-shaped. About 50% to about 75% of the particles are platelet shaped, meaning they are thin in one dimension (thickness) but are larger is the other two dimensions.

The particles have a span of from about 0.1 to 2.1, such as about 0.5 to about 2.0, and about 1.0 to about 2.0. The span is calculated as (d90-d10)/d50. The value for d50 (or the median particle size) is the particle size at the $50^{th}$ percentile of the distribution of particle sizes. The value for d90 is the particle size at the $90^{th}$ percentile of the distribution of particle sizes. The value for d10 is the particle size at the $10^{th}$ percentile of the distribution of particle sizes. The particles size distribution is measured using a Cilas 1064L Laser diffractometer particle sizer. To prepare the sample to be measured, 100 mg of the sample to be measured was dispersed in 9.9 g deionized water by sonicating for 5 min. The sample was loaded into the particle sizer using standard protocols. The particle sizer gives the distribution of the entire sample, including the d10, d50 and d90.

The median particle size, d50, of the particles is in the range of about 1 μm to about 60 μm, such as about 1 μm to about 30 μm and about 1 μm to about 15 μm.

Examples of the substrate include, but are not limited to, fumed alumina, aluminum oxide, aluminum oxide hydrate, aluminum hydroxide, aluminum silicate hydroxide, platy alumina, barium sulfate, bismuth oxychloride, boehmite, calcium aluminum borosilicate, calcium carbonate, clay, collagen, colloidal silica, corundum, diatoms, diatomite, diatomaceous earth, gibbsite, guanine, graphite, hexagonal boron nitride, kaolin, magnesium silicate, natural and synthetic mica, micaceous iron oxide, pyrophyllite, silica, sericite, talc, and mixtures thereof. In some embodiments, the substrate is selected from kaolin, talc, diatomaceous earth, sericite, and calcium carbonite. In some embodiments, the substrate is selected from diatomaceaous earth, talc, mica, alumina, kaolin, calcium carbonate, barium sulfate.

In some embodiments, one or more additives is blended with the soft-focus composition. Examples of the function of these additives include, but are not limited to, improving dispersability, improving the feel, improving the hydrophobicity, improving the oil absorption, etc. Additionally, the additives can modify the surface charge characteristics of the soft-focus composition to be cationic, anionic, neutral or uncharged.

It has been found that the ability of a particle to uniformly scatter light in all directions while limiting the amount of directly reflected and transmitted light produces a soft-focus effect. The soft-focus effect is highly desirable in personal care, cosmetic, or skin care formulations as it can impart an illusion of youth when used in skin care formulations.

A soft-focus effect is created when a composition comprising a particle that has a $SFF_T$ of from about 0.35 to about 0.7 and a $SFF_R$ of from about 0.4 to about 0.7, is applied to a surface, film, or filter. It has been found that when the transmission soft-focus factor ($SFF_T$) and the reflectance soft-focus factor ($SFF_R$) of a particle are within this range, the composition comprising the particle creates a soft-focus effect. While others have described creating a soft-focus effect, it may be a different or weaker optical effect that does not have the required $SFF_R$ and $SFF_R$ requirements.

Additionally, the composition achieves this level of soft-focus without the use of synthetic mineral materials. Synthetic polymers of polymethylmethacrylate (PMMA), polyethylene, polyamide, and/or silicone elastomer have been used by others (U.S. Pat. No. 6,511,536; US 2008/0219940; and U.S. Pat. No. 7,709,013) to create a soft-focus effect. However, these materials are not naturally derived and are not biodegradable. In addition, these synthetic "microbeads" are undesirable because they may persist in the environment and not readily breakdown leading to environmental build-up.

The described soft-focus effect has a required amount of diffusely transmitted and reflected light, i.e. light that is transmitted in directions that are away from the direction of the incident beam of light. In some embodiments, the diffusely transmitted and reflected light is equal in all angles. If the soft-focus composition has a high amount of diffuse transmission but a low amount of diffuse reflection, then it would be glossy and would draw attention to wrinkles and imperfections. If the soft-focus composition has a high amount of diffuse reflection but a low amount of diffuse transmission, then the soft-focus composition would conceal or whiten the natural color of the skin, causing it to appear artificial or fake.

Formula 1 calculates a soft-focus factor that is used to evaluate the transmission properties of a soft-focus composition. The soft-focus composition is measured in a paint film formed by drawing it down on a Mylar transparency.

$$SFF_T = \%T_{TOT} * \%T_{DIF} \quad \text{(Formula 1)}$$

The transmission soft-focus factor is $SFF_T$. The total average transmittance of the display between the wavelengths of 400 nm to 700 nm is % $T_{TOT}$; which is defined as the total combined transmittance of the specular (within 8° of the incident beam) and diffused light. The total average diffuse transmittance of the display between the wavelengths of 400 nm to 700 nm (specular transmittance excluded) is % $T_{DIF}$. Materials that have a large $SFF_T$ indicate that they have a maximized combination of total and diffuse transmission, which means that the measured material is too opaque for a good soft-focus effect.

Formula 2 calculates a soft-focus factor that is used to evaluate the light reflection properties of a soft-focus composition. The soft-focus composition is measured in a paint film formed by drawing it down on a black and white sheet of paper (e.g. Byk Chart 2811).

$$SFF_R = L*75/L*15 \quad \text{(Formula 2)}$$

The reflection soft-focus factor is $SFF_R$. The CIELab brightness at 75° from the specular reflection at a 45° incident beam angle is L*75. The CIELab brightness at 15° from the specular reflection at a 45° incident beam angle is L*15. Materials that have a large $SFF_R$ indicate that there is generally an even distribution of diffusely reflected light at all measurement angles.

In some embodiments, the soft-focus composition has a $SFF_T$ value in the range of about 0.35 to about 0.7, when it is tested at 10% loading in a solvent-borne cellulose acetate butyrate paint base. In some embodiments, the soft-focus composition has an $SFF_R$ value in the range of about 0.4 to about 0.7, when it is tested at 5% loading in a solvent-borne cellulose acetate butyrate paint base. To be clear the composition has these $SFF_T$ and $SFF_R$ values when tested at 10% loading in a solvent-borne cellulose acetate butyrate paint base, but may be used at different loading and with other bases. It is the combination of $SFF_R$ and $SFF_T$ falling within these ranges that provides a soft-focus composition with the proper combination of hiding power and transparency.

The surface of human skin is characterized by the presence of fine lines, wrinkles, freckles and/or blemishes. The presence of too many of any of these characteristics can be perceived as a defect and therefore there is a need for temporary solutions to conceal these defects to impart an impression of youth. One technology that is used to camouflage these defects imparts a characteristic known commonly as soft-focus. Soft-focus is an optical effect whereby small imperfections are blurred, giving skin a smooth appearance with a glow that are commonly associated with youth.

The soft-focus composition can be used in personal care, cosmetic, or skin care formulations to impart a soft-focus effect on the skin to hide fine lines and blemishes while allowing the natural glow of the skin to shine through.

In some embodiments, the soft-focus composition is incorporated into any type of personal care, cosmetic, or skin care formulation at an optimized loading that shows maximum soft-focus. The optimized loading of the soft-focus composition in the chosen vehicle can be determined by plotting $SFF_R$ versus $SFF_T$, where $SFF_R$ and $SFF_T$ are the x- and y-axis, respectively. When these values are plotted at different pigment loadings, a peak emerges in the plot that represents the ideal loading for soft-focus for the soft-focus composition that is used. This phenomenon is shown graphically in FIG. 1. In one embodiment, the loading of the soft-focus pigment system is in the range of about 0.1% to about 20.0% by weight with regards to the total weight of the personal care or cosmetic formulation.

Examples of personal care formulation include, but are not limited to, acne treatments, face creams, skin gels, hand creams, body lotions, moisturizers, water in oil formulation, oil in water formulations, cellulite treatments, body splashes, shampoos, conditioners, styling products, hair sprays, setting lotions, primers, mousses, gels, pomades, waxes, dry shampoos, serums, oils, hair color, root touch up products, scalp treatments, deodorants, antiperspirants, sun screens, tanning lotions, skin lighteners, lip balms, anti-aging creams, eye serums, body oils, make up removers, shaving creams, shaving gels, and eye creams.

Examples of cosmetic formulations include, but are not limited to foundations, pressed powders, loose powders, bronzers, concealers, eye shadows, eye liners, lipsticks, lip glosses, blushes, rouges, facial powders, and nail polishes.

In some embodiments, a cosmetic formulation comprises the soft-focus composition at a loading in the range of about 0.1% to about 90% with respect to the total weight of the skin care formulation, such as 0.1% to about 20%. The cosmetic formulation may comprise one or more ingredient types from the following list: liquid diluents, powder dilutants, chelating agents, humectants, rheology modifiers, emulsifiers, co-emulsifiers, synergists, emollients, UV filters, thickeners, preservatives, desurfactants, detergents, conditioning agents, stabilizers, stabilizing polymers, fillers, structurants, neutralizers, vitamins, minerals, pearlizing agents, botanical extracts, antioxidants, occlusive, skin feel enhancers, powdered fillers, waxes, oils, mineral oils, shine enhancers, fragrances, binders, dry binders, dyes, inorganic pigments, organic pigments, effect pigments, pearlescent pigments, and combinations thereof.

In some embodiments, the soft-focus pigment system can be used to impart a soft-focus effect on all types of skin types, tones, shades, and blemishes.

In some embodiments, a skin care formulation comprises the soft-focus composition at a loading in the range of about 0.1% to about 20% with respect to the total weight of the skin care formulation. The skin care formulation may contain one or more ingredient types from the following list: dilutants, thickeners, rheology modifiers, emollients, film forming agents, occlusive, exfoliants, fillers, neutralizers, emulsifiers, structurants, anti-irritants, anti-acne medications, solvents, moisturizers, skin conditioning agents, co-emulsifiers, synergists, fragrance, botanical extracts, preservatives, brightening agents, ultraviolet light filters, ultraviolet light stabilizers, detergents, conditioning agents, tanning agents, humectants, mineral oils, revitalizers, polymeric oils, waxes, amino acids, proteins, enzymes, vitamins, minerals, chelating agents, antioxidants, foaming agents, defoamers, dyes, inorganic pigments, organic pigments, effect pigments, pearlescent pigments, and other additives and ingredients known to those skilled in the art.

In some embodiments, personal care, cosmetic formulation, or skin care formulation may additionally comprise light diffusing or colored pigments. Light diffusing and colored pigments are discussed below.

In some embodiments, the soft-focus composition is incorporated into an ink or coating. The ink or coating created may add a light scattering effect that has been deemed desirable. The soft-focus effect of the coating or ink can create a variety of effects including but not limited to opacification, matting, hazing, and extending. Examples of inks and coatings include, but are not limited to, automotive coatings, protective clear coatings, interior architectural coatings, exterior architectural coatings, powder coatings, industrial coating, gravure inks, flexographic inks, paste inks, energy curing (UV or EB) inks, etc. Additionally, the soft-focus composition may be used in combination with effect pigments or organic pigments. In some embodiments, the ink or coating comprises about 0.1% to about 50% of the soft-focus composition by weight, such as about 1% to about 40% by weight.

The coating or ink composition is obtained by blending the soft-focus composition with a coating resin. The coating resin may be dispersed in a solvent or may be used as a dry powder as in the case of powder coatings. Examples of coating resins include, but are not limited to epoxy, polyester, polyurethane, polyvinyl, cellulose, polyamide, nitrocellulose, acrylic, alkyd, fluorinated resins and the like.

In some embodiments, the coating or ink composition it can be used in conjunction with one or more additional light diffusing or colored pigments. Examples of another light diffusing particle include platelet-shaped boron nitride, flaky alumina, spherical alumina, spherical silica, pearlescent pigments, nylon-12, polyethylene, polymethylmethacrylate, polystyrene, silicone crosspolymer particles, titanium dioxide, zinc oxide, and mixtures thereof. If an additional colored pigment is used, then it can be either an organic pigment, an inorganic pigment, a metallic pigment, a pearlescent pigments, and mixtures thereof.

Examples of additional colored pigment include organic pigments such as, azo pigments, polycylic pigments, anthraquinone pigments including monoazo pigments, disazo pigments, disazo condensation pigments, naphthol pigments, benzimidazolone pigments, isoindolinone pigments, isoindoline pigments, metal complex pigments, quinacridone pigments, perylene pigments, carbon black pigments, phthalocyanine pigments, perinone pigments, diketopyrrolo-pyrrole pigments, thioindigo pigments, anthropyrimidine pigments, flavanthrone pigments, anthanthrone pigments, dioxazine pigments, triarylcarbonium pigments, quinophthalone pigments, and combinations thereof.

Examples of additional colored pigment include inorganic pigments such as, titanium oxides, iron oxides, vanadium oxides, chromium oxides, manganese oxides, tungsten oxides, cadmium sulfides, zinc sulfides, cadmium mercury sulfides, iron sulfides, aluminosilicates, aluminum oxides, cerium oxides, spinel pigments, lanthanum hexaborides, and mixtures and alloys thereof.

Examples of additional colored pigment include metallic pigments. In some embodiments, the metallic pigment is platelet shaped with a diameter (d50) in the range of about 1 μm to about 150 μm. Examples of metals in the platelet shaped metallic pigments include, but are not limited to, aluminum, copper, iron, stainless steel, zinc, silver, titanium, gold, magnesium, zinc-copper alloys, zinc-aluminum alloys, zinc-magnesium alloys, silver-plated glass flakes, and mixtures and alloys thereof.

Examples of additional colored pigment include pearlescent pigments. Pearlescent pigments comprise a transparent, non-metallic, platelet-shaped substrate that is coated with one or more layers comprising metal oxides having refractive indices. The pearlescent pigment can be either single or multilayered and has an interference color when viewed over a black background. Examples of the interference color of the pearlescent pigment include, but are not limited to, silver, yellow, gold, cyan, magenta, red, blue, green, violet, and shades of the aforementioned.

Examples of the non-metallic platelet substrate of a pearlescent pigment include, but are not limited to natural mica, synthetic mica, bismuth oxychloride, graphite, aluminum oxide, micaceous iron oxide, perlite, silicon dioxide, titanium dioxide-coated mica and iron oxide-coated mica, among others. The size of the platelet-shaped substrate is not critical and depends on the end use of the pigment. In general, the diameter of the platelet-shaped substrate can be in the range of, but is not limited to, about 1 μm to about 500 μm and the thickness of the platelet-shaped substrate can be in the range of, but is not limited to, about 5 nm to about 1 μm.

Examples of metal oxides used to coat the non-metallic platelet substrate of a pearlescent pigment include, but are not limited to, silicon dioxide, titanium dioxide, zinc oxide, zirconium dioxide, tin oxide, cerium dioxide, vanadium (IV) oxide, manganese oxide, lead oxide, chromium oxide, iron oxide, aluminum oxide, tungsten oxide, and mixtures and alloys thereof. In some embodiments, the coating comprises a hydrated oxide of any one of the aforementioned oxides. In some embodiments, the coating is a doped oxide of any one of the aforementioned oxides. In some embodiments, the metal oxide layer is colorless. The thicknesses of the metal oxide layers are variable but must be at least partially transparency. In some embodiments, the thickness of the metal oxide layers ranges from about 20 nm to about 350 nm.

In some embodiments, a coating comprising the soft-focus composition additionally comprises an additive selected from a crosslinker, water, an organic solvent, an interfacial active agent, a hardener, an ultraviolet absorber, a thickener, a corrosion inhibitor, and mixtures thereof.

In some embodiments, an ink comprising the soft-focus composition may be a solvent borne, waterborne, heatset or energy curable ink. A packaging ink comprising the soft-focus composition may be used to color the interior of a package, the exterior of a package, or both. In some embodiments, an ink comprising the soft-focus composition may be a flexographic ink, screen ink, paste ink, sheetfed ink, energy cured ink, gravure ink, or ink-jet ink.

While the present disclosure has illustrated by description several embodiments and while the illustrative embodiments have been described in considerable detail, it is not the intention of the applicant to restrict or in any way limit the scope of the appended claims to such detail. Additional advantages and modifications may readily appear to those skilled in the art.

EXAMPLES

Example 1

In a jacketed 1 L reactor, 22 g of a fine cosmetic diatomaceous earth (Imercare 266D, Imerys) was dispersed in 151 g isopropanol and stirred at 400 RPM. To this slurry, 49.9 g titanium tetrabutoxide was added. The reactor was heated to reflux and a solution of 3% $NH_4OH$ in water (25.6 g) was slowly added at 0.2 mL/min. Once the addition was complete, the solution was stirred at reflux for an additional hour. After this time, the slurry was filtered, washed with isopropanol, and dried at 60° C. for several hours. A free flowing white powder was produced.

Example 2

In a jacketed 1 L reactor, 37.5 g of a fine cosmetic talc (MP1538, Minerals Technologies) was dispersed in 220 g deionized water. The slurry was stirred at 500 RPM and heated to 80° C. The pH of the slurry was adjusted to 1.8 with 10%0/HCl. Once the temperature was reached, 50 g of a 15% solution of $TiOCl_2$ in HCl was added at 0.2 mL/min. Separately, but concurrently, a 7.5% solution of NaOH was added in order to maintain a pH of 1.8. Once all of the $TiOCl_2$ was added, the NaOH addition was halted and the slurry was stirred for 1 hour. The slurry was filtered and rinsed with deionized water and dried at 60° C. overnight. A free flowing white powder was produced.

Example 3

In a jacketed 1 L reactor, 20 g of a fine cosmetic talc (MP1538, Minerals Technologies) was dispersed in 220 g deionized water. The slurry was stirred at 500 RPM and heated to 80° C. The pH of the slurry was adjusted to 1.8 with 10% $H_2SO_4$. Once the temperature was reached, 53.3 g of a 15% solution of $TiO(SO_4)$ in $H_2SO_4$ was added at 0.2 mL/min. Separately, but concurrently, a 7.5% solution of NaOH was added to maintain the pH at 1.8. After all the $TiO(SO_4)$ was added, the NaOH addition was halted and the slurry is stirred for 1 hour. The slurry was filtered and rinsed with deionized water followed by ethanol and dried at 60° C. overnight. Following drying, the material was calcined at 500° C. for 3 hrs. A free flowing white powder was produced.

Comparative Example 4

Commercial talc (MP1538, Minerals Technologies).

Comparative Example 5

A blend was prepared by intimately mixing 7.5 g of Example 5 and 2.5 g of Example 9 until uniform.

Comparative Example 6

Commercial product SunMica Fine White (Sun Chemical), which is $TiO_2$ coated mica.

Comparative Example 7 (an Unlayered Pigment)

The commercial product Trés BN 3016 (Saint-Gobain).

Comparative Example 8 (an Unlayered Pigment)

The commercial product T#7071 $TiO_2$ (Kronos).

Comparative Example 9

In a jacketed 1 L reactor, 37.5 g of a coarse talc (Microtalc BP-210) is dispersed in 220 g deionized water. The slurry is stirred at 500 RPM and heated to 80° C. The pH of the slurry is adjusted to 1.8 with 10% HCl. Once the temperature has been reached, 50 g of a 15% solution of $TiOCl_2$ in HCl is added at 0.2 mL/min. Separately, but concurrently, a 7.5% solution of NaOH is added in order to maintain a pH of 1.8. Once all of the $TiOCl_2$ is added, the NaOH addition is halted and the slurry is stirred for 1 hour. The slurry is filtered and rinsed with deionized water and dried at 60° C. overnight. A free flowing white powder is produced that shows little to no soft focus effect.

Example 10: Evaluation of the Optical Properties of the Pigments

The previous examples were dispersed into a solvent-borne cellulose acetate butyrate paint base at 1%, 2.5%, 5%, and 10% (w/w) loadings. These paints were drawn down using a 1.5 mil Byrd applicator onto a black and white test card (Byk Chart 2811). An additional drawdown was made on a Mylar sheet. The five-angle color data was measured over the black portion of the card using an X-Rite MA-98 spectrophotometer.

For direct and indirect transmittance measurements, the samples drawn down on the Mylar sheets were used and the total and direct transmittance in the wavelength range of 400 nm to 700 nm was measured using an X-Rite Color i7. The diffuse transmittance (% $T_{DIF}$) was calculated by subtracting the direct transmittance from the total transmittance (% $T_{TOT}$). The $SFF_T$ and $SFF_R$ were calculated using equations 1-2.

Table 1 shows the $SFF_T$ and $SFF_R$ values for each material at a 10% (w/w) loading. Examples 1-4 all show $SFF_T$ and $SFF_R$ values in the ranges of about 0.35 to about 0.6 and 0.4 to about 0.7, respectively. Comparative Examples 4-6 and 8-9 do not have $SFF_T$ and $SFF_R$ values that fall within the disclosed ranges. Finally, Examples 1-3 all perform similar to the unlayered pigment of Comparative Example 7.

TABLE 1

$SFF_T$ and $SFF_R$ values for films at 10% (w/w) loading

| Example | $SFF_T$ | $SFF_R$ | d10 | d50 | d90 | Span |
|---|---|---|---|---|---|---|
| Example 1 | 0.49 | 0.50 | 3.3 | 14.3 | 26.9 | 1.7 |
| Example 2 | 0.41 | 0.61 | 1.7 | 5.0 | 11.2 | 1.9 |
| Example 3 | 0.46 | 0.58 | 1.5 | 4.9 | 11.2 | 2.0 |
| Example 4 (comp.) | 0.31 | 0.16 | 3.3 | 9.5 | 18.7 | 1.6 |
| Example 5 (comp.) | 0.45 | 0.81 | 0.3 | 6.9 | 18.5 | 2.6 |
| Example 6 (comp.) | 0.11 | 0.24 | 4.5 | 9.3 | 17.0 | 1.4 |
| Example 7 (comp.) | 0.57 | 0.49 | 7.0 | 20.3 | 45.3 | 1.9 |
| Example 8 (comp.) | 0.25 | 0.94 | 0.3 | 1.1 | 3.0 | 2.4 |
| Example 9 (comp.) | 0.52 | 0.29 | 3.5 | 22.1 | 82.0 | 3.6 |

FIG. 1 shows the relationship between the calculated $SFF_T$ and $SFF_R$ values for the examples at different pigment loadings. From the graph it is apparent that it is not the $SFF_T$ or $SFF_R$ individually that produce a desirable soft-focus affect, but rather a ratio of the two parameters. Materials that strongly reflect diffuse light and possess a $SFF_R$ value above the preferred range become opaque and unnatural looking on the skin. In contrast, materials with a $SFF_R$ value below the preferred range are generally more transparent but reflect light in a specular direction, giving an unnatural, glossy appearance. The soft-focus composition has good diffuse reflection with a high degree of transparency. The same is true for the $SFF_T$ value. Materials that are highly transparent and possess a $SFF_T$ value above the preferred range will not reflect light to the extent required to reduce surface blemishes. Alternately, materials that lack diffuse transmission and possess a $SFF_T$ value below the preferred range will not blur and scatter light appropriately.

Example 11: Personal Care Formulations

Soft-focus compositions were formulated into personal care formulations. The recipe of this formulation is described in Table 2. The materials are added under agitation in the order listed until uniform. A wrinkle reducing body lotion is produced. These lotions were tested on BIOSKIN Plate BP-EV1, which simulates skin and wrinkles in varying degrees of wrinkle intensity. The wrinkle intensity scale goes from 1 for average skin texture, to 6 for extreme skin texture and wrinkles. Table 3 shows the maximum wrinkle intensity that is hidden by the lotion containing the pigment system.

TABLE 2

Personal Care Formulation

| Ingredient | % (w/w) |
|---|---|
| Water | 90.1 |
| Hydroxyethyl Acrylate/Sodium Acryloyldimethyl Taurate Copolymer & Polyisobutene & PEG-7 Trimethylolpropane Coconut Ether | 1.0 |
| Capric/Caprylic Triglycerides | 2.00 |
| Tocopherol | 0.05 |
| Dimethicone (200 cstks) | 4.00 |
| Disodium EDTA | 0.05 |

TABLE 2-continued

Personal Care Formulation

| Ingredient | % (w/w) |
|---|---|
| Propylparaben | 0.10 |
| Methylparaben | 0.20 |
| Soft-focus composition - see Table 3 | 2.5 |
| Total | 100.00 |

TABLE 3

Maximum wrinkle intensity that is hidden by the lotion containing the pigment system

| Soft-focus Pigment System | Wrinkle Hiding Power |
|---|---|
| Example 2 | 5 |
| Example 4 (comp.) | 1 |
| Example 7 (comp.) | 4 |

The examples were applied in a transparent film on the BIOSKIN plate to examine wrinkle-hiding power. Comparative Example 5 and 8 leave an opaque film that was visible even after the lotion dries, creating an unnatural appearance. The opaqueness of other pigments may in fact draw attention to the texture of skin rather than the desired effect of hiding imperfections. In this way, the soft-focus composition performs better than previous soft-focus materials by providing a composition that hides skin imperfections while imparting a natural look but to the absence of specular luster as seen in laminar pigments allowing for a more natural blurring effect on the skin.

Those skilled in the art having the benefit of the teachings of the present invention as hereinabove set forth, can effect numerous modifications thereto. These modifications are to be construed as being encompassed within the scope of the present invention as set forth in the appended claims.

What is claimed is:

1. A soft-focus composition comprising particles, wherein the particles comprise a substrate with a metal oxide coating;
    wherein the metal oxide coating covers from about 50% to about 75% of the surface area of the substrate;
    wherein the particles have a span of from about 0.1 to about 2.1; and
    wherein from about 50% to about 75% of the particles are platelet shaped and the remainder are at least one different shape.

2. The soft-focus composition of claim 1, wherein the particle has a $SFF_T$ of from about 0.35 to about 0.7 and a $SFF_R$ of from about 0.4 to about 0.7, when it is tested at 10% loading in a solvent-borne cellulose acetate butyrate paint base.

3. The soft-focus composition of claim 1, wherein the substrate is selected from fumed alumina, aluminum oxide, aluminum oxide hydrate, aluminum hydroxide, aluminum silicate hydroxide, barium sulfate, bismuth oxychloride, boehmite, calcium aluminum borosilicate, calcium carbonate, clay, collagen, colloidal silica, corundum, diatoms, diatomite, diatomaceous earth, gibbsite, guanine, graphite, hexagonal boron nitride, kaolin, magnesium silicate, natural and synthetic mica, micaceous iron oxide, pyrophyllite, silica, sericite, talc, and mixtures thereof.

4. The soft-focus composition of claim 1, wherein the particle has a median particle size d50 from about 1.0 µm to about 60 µm.

5. The soft-focus composition of claim 1, wherein the at least one different shape of the particles comprises spheroids, cylinders, polygons, potato-shaped, octahedral, hedgehog, and star-shaped particles.

6. The soft-focus composition of claim 1, wherein the metal oxide coating comprises a layer selected from aluminum oxide, bismuth oxide, cerium oxide, chromium oxide, iron (II) oxide, iron (II, III) oxide, iron (III) oxide, magnesium silicate, silicon dioxide, titanium dioxide, zinc oxide, zirconium oxide, and mixtures or alloys thereof.

7. The soft-focus composition of claim 1, wherein the metal oxide coating comprises from about 5% to about 75% of the total particle mass.

8. The soft-focus composition of claim 1, wherein the thickness of the metal oxide coating is from about 10 nm to about 1000 nm.

9. The soft-focus composition of claim 1, further comprising a pigment.

10. The soft-focus composition of claim 9, wherein the pigment is selected from azo pigments, polycylic pigments, anthraquinone pigments, disazo pigments, disazo condensation pigments, naphthol pigments, benzimidazolone pigments, isoindolinone pigments, isoindoline pigments, metal complex pigments, quinacridone pigments, perylene pigments, carbon black pigments, phthalocyanine pigments, perinone pigments, diketopyrrolo-pyrrole pigments, thioindigo pigments, anthropyrimidine pigments, flavanthrone pigments, anthanthrone pigments, dioxazine pigments, triarylcarbonium pigments, quinophthalone pigments, and combinations thereof.

11. The soft-focus composition of claim 9, wherein the pigment is selected from titanium oxides, iron oxides, vanadium oxides, chromium oxides, manganese oxides, tungsten oxides, cadmium sulfides, zinc sulfides, cadmium mercury sulfides, iron sulfides, aluminosilicates, aluminum oxides, cerium oxides, spinel pigments, lanthanum hexaborides, and mixtures or alloys thereof.

12. A personal care or cosmetic composition comprising the soft-focus composition of claim 1.

* * * * *